US006934022B1

(12) United States Patent
Engelhardt

(10) Patent No.: US 6,934,022 B1
(45) Date of Patent: Aug. 23, 2005

(54) METHOD FOR DIFFERENTIATED INVESTIGATION OF DIVERSE STRUCTURES IN PREFERABLY BIOLOGICAL PREPARATIONS

(75) Inventor: Johann Engelhardt, Bad Schoenborn (DE)

(73) Assignee: Leica Microsystems Heidelberg GmbH, Mannheim (DE)

( * ) Notice: Subject to any disclaimer, the term of this patent is extended or adjusted under 35 U.S.C. 154(b) by 0 days.

(21) Appl. No.: 09/857,960

(22) PCT Filed: Dec. 10, 1999

(86) PCT No.: PCT/DE99/03946

§ 371 (c)(1),
(2), (4) Date: Jun. 12, 2001

(87) PCT Pub. No.: WO00/36450

PCT Pub. Date: Jun. 22, 2000

(30) Foreign Application Priority Data

Dec. 17, 1998 (DE) ................................ 198 58 431
Oct. 22, 1999 (DE) ................................ 199 50 909

(51) Int. Cl.[7] ...................... G01N 15/02; G01N 21/00; G01N 21/55
(52) U.S. Cl. ...................... 356/336; 356/337; 356/432; 356/445
(58) Field of Search .............................. 356/335, 336, 356/337, 39, 316, 317, 417, 340, 433–436, 356/440, 441, 442, 445–448, 432; 604/6.08; 422/52, 55, 68.1, 82.08, 82.05; 436/518, 436/172; 250/458.1, 459.1, 461.1, 461.2, 250/462.1; 382/128–134

(56) References Cited

U.S. PATENT DOCUMENTS

| 4,169,676 A | * | 10/1979 | Kaiser ........................... 356/39 |
| 4,752,567 A | * | 6/1988 | De Brabander et al. ...... 435/7.2 |
| 5,018,209 A | * | 5/1991 | Bacus ........................... 382/129 |
| 5,592,571 A | * | 1/1997 | Peters ........................... 382/261 |
| 5,599,668 A | * | 2/1997 | Stimpson et al. .............. 435/6 |
| 5,843,651 A | | 12/1998 | Stimpson et al. .............. 435/6 |
| 6,180,415 B1 | * | 1/2001 | Schultz et al. ............... 436/518 |
| 6,214,560 B1 | * | 4/2001 | Yguerabide et al. ......... 435/7.1 |

FOREIGN PATENT DOCUMENTS

| EP | 0 254 430 | | 1/1988 |
| EP | 0 326 375 | | 8/1989 |
| EP | 0 469 377 | | 2/1992 |
| EP | 0 822 407 | | 2/1998 |
| WO | WO 98/04740 | * | 2/1998 |
| WO | WO 98/10289 | * | 3/1998 |
| WO | WO 99/13319 | | 3/1999 |

* cited by examiner

Primary Examiner—Zandra V. Smith
Assistant Examiner—Gordon J. Stock, Jr.
(74) Attorney, Agent, or Firm—Simpson & Simpson, PLLC

(57) ABSTRACT

The invention relates to a method for examining different structures in preferably biological preparations in a differential manner, especially by means of confocal laser scanning microscopy. The method is characterized in that particles having a specific diameter and specific characteristics are assigned to the structures and in that said structures are detected by detecting the particles which have specifically bonded in or to the preparations. The detection process is carried out in an advantageous manner by marking the structures with metal particles with diameters of 10 nm to 1,500 nm and detecting Mie scattering or a plasmon signal.

21 Claims, 1 Drawing Sheet

METHOD FOR DIFFERENTIATED INVESTIGATION OF DIVERSE STRUCTURES IN PREFERABLY BIOLOGICAL PREPARATIONS

CROSS REFERENCE TO RELATED APPLICATIONS

The present application is the U.S. national phase under 35 U.S.C. 371 of International Application No. PCT/DE99/03946 filed Dec. 10, 1999 claiming priority of German Patent Application No. 198 58 431.8 filed Dec. 17, 1998 and German Patent Application No. 199 50 909.3 filed Oct. 22, 1999.

FIELD OF THE INVENTION

The invention relates to a method for the differentiated examination of various structures in preferably biological preparations, in particular via confocal laser microscopy.

BACKGROUND OF THE INVENTION

Fundamentally, this involves a detection/marking method, in particular a method as is applied within the context of conventional fluorescence microscopy within the biomedical field. However, the fluorescence microscopy previously employed is in practice exceptionally problematic, particularly since the fluorescent dies used therein fade over time, and specifically have a fading characteristic that prevents the reproduction of examinations. Because of this fading characteristic, the fluorescence intensities change even during the course of microexamination and in particular when there is radiation of the fluorescent die with excitation light. This not only makes a reproduction of the examination impossible, but, what is more, it also makes any examination subsequent to radiation of the biological/medical preparation more difficult or—in terms of a reliable evaluation—makes such an examination nearly impossible.

BRIEF SUMMARY OF THE INVENTION

The objective of the present invention is therefore to configure a method of the type in question for differentiated examination of various structures in preferably biological preparations, in particular via confocal laser scanning microscopy, such that the reproduction of the marking or of the result of the examination is ensured, even after prolonged radiation. The problems occurring in fluorescence microscopy or in connection with fluorescent die binding are to be thereby prevented.

This objective is met via a method for the differentiated examination of various structures in preferably biological preparations, in particular using a confocal laser scanning microscope, as described and claimed herein. Accordingly, the method for differentiated examination of various structures in preferably biological preparations is characterized in that particles with a specific diameter and specific characteristics are assigned to the structures, and said structures are detected by detection of the particles specifically bound in or on the preparations.

In an advantageous manner the particles are detected by virtue of the wavelength of the appropriate light being selected as a function of the diameter and the specific characteristics of the particles such that the particles can be detected on the basis of the Mie scatter or Mie reflexes occurring on the particles.

Alternatively, the particles are also detectable via detection of the plasmon signal of the particles.

BRIEF DESCRIPTION OF THE DRAWINGS

The nature and mode of operation of the present invention will now be more fully described in the following detailed description of the invention taken with the accompanying drawing figure, in which.

DETAILED DESCRIPTION OF THE INVENTION

Figure 1:
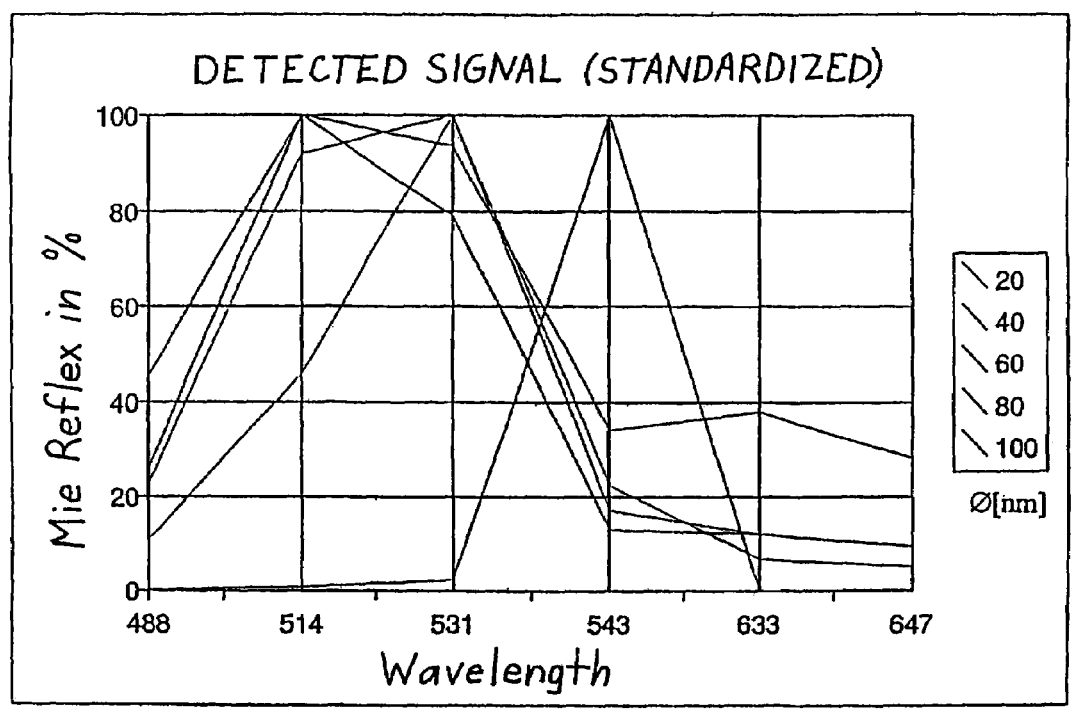
FIG. 1 is a graph showing the reflexes detectable on the basis of the Mie scatter for specific particle diameters, namely for diameters of 20 nm, 40 nm, 60 nm, 80 nm and 100 nm, as a function of the wavelength of the illumination light.

According to the invention, it has been recognized that the problem occurring within the context of fluorescence microscopy is mainly attributable to the fading characteristic of the usable fluorescent dye. According to the invention, there is a deviation from the marking method typically used in the biomedical field; specifically, the structures involved in the preparation are not marked with any kind of dyes, but with particles having a specific diameter and specific material characteristics. While the fluorescent dye attachment depends on the fluorescence behavior of the fluorescent dyes assigned to the structures, the optical characteristics of the particles at some point play no role. What's more, this depends on the diameter and the material characteristics of the particles.

The particles are thus—insofar as required—assigned to the structures or areas of the preparations in question, it being possible to provide the particles with binding means that with certain structures can enter into a chemical bond based on adhesion. A purely mechanical bond is also conceivable. After the particles are assigned to the structure or structures involved, the structure or structures involved are detected via detection of the particles bound in or on the preparations and thus to the structures in question. In concrete terms, the structures or various areas in the preparations are differentiated in that the wavelength of the appropriate light is selected as a function of the diameter and the specific characteristics of the particles such that the particles can be detected on the basis of the Mie scatter occurring on the particles.

Consequently, in a manner according to the invention, a physical phenomenon that is characterized in the technical literature as "Mie scatter" is used. Reference is made here, to cite just one example, to G. Mie, *Ann. Physik* 3, 377 (1908). As far as the theoretical reasons regarding the Mie scatter are concerned, reference is made, moreover, to P. Török et al. "Polarized Light Microscopy" SPIE vol. 3261, pp. 22 and following (1998). Included under the phenomenon characterized as Mie scatter or Mie reflex by the physician G. Mie is a scattering of light on particles, the scatter intensities increasing in the forward direction more strongly than in the reverse direction when the diameter of the particles grows. In contrast to the Rayleigh scatter, the Mie scatter is a function of both the material characteristics (dielectric constant, electrical conductivity) and the diameter of the scattering particles.

At this point it should be particularly stressed that the marking of areas or structures for their differentiated examination by assignment of particles to these structures and by subsequent detection of the particles, said particles being detected by utilization of the Mie scatter occurring on the particles. The phenomenon of the Mie scatter is thus used in a manner according to the invention to detect the particles assigned to the structures and thus to detect the structures themselves.

Instead of detection through Mie scatter occurring on particles, said particles can also be detected by detection of the plasmons signals. Plasmons have already been known from the literature for a long time. What is involved here is a phenomenon from the field of solid-state physics in which the electrons in the conduction band of a solid make vibrations that can be induced by, for example, light of an appropriate wavelength. This has been used primarily so far in connection with measuring devices that are based on the surface-plasmons-resonance effect. Reference is only made, for example, to US patent specification U.S. Pat. No. 5,351,127 in which a corresponding arrangement is described. However, for light microscopy in the classical sense, the production and detection of surface plasmons according to the previously cited publication cannot be used.

Within the context of the previously cited alternative detection of particles by detection of the plasmon signal, surface- or volume-plasmon resonances of the particles that are specifically tied to the structure to be detected are stimulated with appropriate light in a conventional or confocal laser scanning microscope. The surface or volume plasmon resonances thus stimulated are then detected using suitable means. A specific detection of the various particles is possible as a function of the characteristic of the light used and the qualities of the particles used. For example there are available in spherical particles only a limited number of surface plasmons that depend on the diameter, the electron density and the dielectric characteristics of the particles.

Linear polarized light of a specifiable wavelength is used in an advantageous manner in order to be able to use or detect specifically the Mie effect or the Mie scatter occurring on the particles especially well. This is especially true if the wavelength of the light is larger than or approximately equal to the diameter of the particles.

In an especially advantageous manner, the wavelength of the light could be within the range between 300 nm and 1,500 nm. The size of particles could be below the optical resolution. In concrete terms, this means a particle diameter in the range between 10 nm and 1,000 nm is needed in order to be able to optimally use specifically the Mie scatter for the detection of the particles.

In a likewise advantageous manner, the wavelength of the light—for a given particle size and given specific characteristics of the particles—is selected such that a maximum Mie reflex can be detected. Starting with the theoretical reasons that are foundational here and literature references cited at the outset, reference is made on this to FIG. 1 or to the graphic there, which shows the reflexes detectable on the basis of the Mie scatter for specific particle diameters, namely for diameters of 20 nm, 40 nm, 60 nm, 80 nm and 100 nm, as a function of the wavelength of the illumination light. According to this illustration, for given particle sizes those wavelengths of the light can be selected for which—for a specific particle of a given diameter—a maximum Mie reflex or a maximum Mie scatter is provable and therefore detectable.

It is theoretically possible that not just one area of the preparation is provided with a type of particle—of equal diameter and of equal characteristics—but rather that areas of the preparation differentiated from each other are provided with particles of varying diameter, so that the areas are simultaneously detectable via appropriate light of various wavelengths. It is also possible to provide the areas of the preparation to be differentiated with particles of various specific characteristics—for different or equal diameters—so that the areas are simultaneously detectable via corresponding light of different or equal wavelengths. Both variants can be realized to differentiate between various areas of the preparation.

The particles used for marking are preferably metal particles, and specifically on the basis of their dielectric constant and electrical conductivity. The particles can also be particles metalized on the surface. The particles are furthermore configured preferably as ellipsoids or beads, specifically in order to maintain a homogeneous Mie scatter on the particles.

The particles can be detected via the Mie scatter or the Mie reflexes occurring there using a microscope, and specifically in both transmission microscope mode and in reflection microscope mode. If the detection occurs in transmission microscope mode, then a conventional polarization transmission microscope or a confocal polarization transmission microscope could be used. If the detection occurs in reflection microscope mode, a conventional polarization reflection microscope or a confocal polarization reflection microscope could be used to implement the detection method.

A high-pressure lamp, for example, is a possible light source, and it should preferably have means for selecting the wavelength and polarizing the light. This means for selecting wavelength and polarizing can also be—separately—connected in series to a traditional high-pressure lamp.

In an especially advantageous manner a laser can be used as a light source, especially if confocal laser scanning microscopy is to be employed. In an advantageous manner, this is a laser that emits polarized light of one wavelength. The use of a laser that emits polarized light of several different wavelengths is likewise conceivable, wavelength selecting means being connected in series—integrally or separately—to the laser. Conventional lasers and conventional wavelength-selecting means can be fallback options in this context.

For optimal detection of the Mie signal, it is of additional advantage if an OPO (optical parametric oscillator) connected in series with the laser is used as the light source. As a result it is specifically possible to adjust the lighting wave length almost continually, maximum detection signals being thereby detectable for a specific particle type.

With regard to the analysis of the preparation, it is advantageous if several image recordings are considered specifically in order to be able to eliminate or compensate for errors in picture recording. In this regard a conventional transmitted light microscopic image could also be recorded using the same microscope and taken into consideration in the image evaluation. Digital image processing methods can be used in this case. Nevertheless, systematic errors of the microscope in question can be eliminated or compensated by comparing it to a conventional transmitted light microscopic image.

It is also conceivable that for the analysis of the preparation on a recorded image, a conventional reflection microscopic image is recorded using the same microscope and taken into consideration in the image recording. Also in this case digital processing methods can be used. The processing of a reflection microscopic image is also conceivable, provided that both images are recorded using the same microscope. These images are used for the analysis of the preparation and considered in the image evaluation after employing digital image processing methods.

With regard to the image recording and subsequent image processing, it is of further advantage if several picture recordings are performed under various lighting-/detection angles. These recorded images can also be taken into consideration for image evaluation in order to be able for example to eliminate shadow effects or the like that falsify the analysis or the result. Digital processing methods can also be employed in this case.

The light used to detect the particles and thus for the differentiated examination of various structures can be provided via a single light source, thus, for example, via a laser light source as per the foregoing description. However, it is necessary to provide light with several wavelengths in order to detect particles with various diameters and/or with different characteristics; thus, to this end several light sources that emit light with appropriate wavelengths simultaneously or at different times can be used. In this respect a detection of the particles assigned to the various structures that is simultaneous or at different times is possible.

It has already been mentioned previously that the particles on the one hand can be metallic particles and on the other hand can be particles with a metallic surface. To bind the particles to the preparation or to the structures in question, it is very advantageous if the particles are coated on the surface and if the coating enables a bond to appropriate complementary structures of the preparation. The bond can be achieved mechanically, adhesively or completely chemically.

Finally, it should be emphasized that the method according to the invention has the enormous advantage, compared to the traditional fluorescence microscope, that the particles used for marking—in contrast to the fluorescent dies—do not change over time and during the radiation. Furthermore, the sensors used to detect the Mie scatter or the Mie reflection must not be configured so sensitively as is the case with the fluorescent microscope—for detection of the fluorescence phenomena. If then the preparations or their structures are prepared with the particles used here, additional examinations can be reproduced on the preparations, even after considerable radiation. In any case, it is not the particles used for marking that are problematic in this context, but rather just the consistency of the preparation itself. In any case, in a manner according to the invention it is no longer necessary to be concerned about markings that change over time.

What is claimed is:

1. A method for the differentiated examination of various structures in a biological preparation using a microscope, said method comprising the steps of:
    A) assigning particles with a specific diameter and specific characteristics to said structures;
    B) detecting said structures by detecting said particles specifically bound in or on said structures of said preparation using a light that acts on said particles, said particles possessing constant characteristics independent of the time of irradiation by said light;
    C) simultaneously recording a microscopic image of said detected particles and at least one microscopic image of said structures using the microscope; and,
    D) evaluating said recorded images using digital image processing.

2. The method as recited in claim 1, wherein said particles are detected by selecting a wavelength of a suitable light as a function of said diameter and of said specific characteristics of said particles such that said particles are detected on the basis of a plasmon signal occurring on said particles.

3. The method as recited in claim 1, wherein said light is produced using a laser as a light source, said laser emitting polarized light of one wavelength.

4. The method as recited in claim 1, wherein said light is produced using an optical parametric oscillator as a light source, the wavelength of said light being variable using said optical parametric oscillator, whereby a maximum Mie-signal for a specific particle type can be measured.

5. The method as recited in claim 1, wherein said particles are coated on the surface and the coating enables a specific bonding to corresponding complementary structures of said preparation.

6. The method as recited in claim 1, wherein said microscopic images comprise transmitted light microscopic images.

7. The method as recited in claim 1, wherein said microscopic images comprise reflected light microscopic images.

8. The method as recited in claim 1, wherein said microscopic images comprise a conventional transmitted light microscopic image and a reflected light microscopic image.

9. The method as recited in claim 1, wherein said microscopic images comprise a plurality of transmitted light microscope images and reflected light microscope images, wherein said transmitted light microscope images and reflected light microscope images are obtained under a plurality of lighting and detection angles.

10. The method as recited in claim 1, wherein said particles are metallic particles or particles metalized on the surface.

11. The method as recited in claim 10, wherein said particles are formed as ellipsoids or beads.

12. The method as recited in claim 1, wherein said light is produced using a high-pressure lamp as a light source.

13. The method as recited in claim 12, wherein said light source comprises means for wavelength selection and polarization.

14. The method as recited in claim 1, wherein said light is produced using a laser as a light source, said laser emitting polarized light of several different wavelengths, and means for selecting wavelengths is connected in series to said laser.

15. The method as recited in claim 14, wherein said means for selecting wavelengths is integrally connected in to said laser.

16. The method as recited in claim 1, wherein said particles are detected by selecting a wavelength of suitable light being as a function of said diameter and of said specific characteristics of the particles such that said particles are detected on the basis of a Mie scatter occurring on said particles.

17. The method as recited in claim 16, wherein said wavelength of said light is larger than, or is approximately equal to, said diameter of said particles.

18. The method as recited in claim 16, wherein said particles are detected through the Mie-reflexes occurring there in transmission microscope mode.

19. The method as recited in claim 18, wherein said microscope is a conventional polarization transmission microscope or a confocal polarization transmission microscope.

20. The method as recited in claim 16, wherein the specific detection of the particles is achieved via the Mie-reflexes occurring there in the reflection microscope mode.

21. The method as recited in claim 20, wherein said microscope is a conventional polarization reflection microscope or a confocal polarization reflection microscope.

* * * * *

UNITED STATES PATENT AND TRADEMARK OFFICE
CERTIFICATE OF CORRECTION

PATENT NO. : 6,934,022 B1
DATED : August 23, 2005
INVENTOR(S) : Engelhardt, Johann It is certified that error appears in the above-identified patent and that said Letters Patent is hereby corrected as shown below:

<u>Column 6,</u>
Line 19, delete "conventional".

Signed and Sealed this

Thirteenth Day of December, 2005

JON W. DUDAS
*Director of the United States Patent and Trademark Office*